(12) United States Patent
Ghelli et al.

(10) Patent No.: US 7,666,159 B2
(45) Date of Patent: Feb. 23, 2010

(54) VENOUS RESERVOIR IN AN EXTRACORPOREAL BLOOD CIRCUIT

(75) Inventors: Nicola Ghelli, S. Pietro in Casale (IT); Edgardo Costa Maianti, Mirandola (IT); Roberto Balanzoni, San Giovanni Del Dosso (IT)

(73) Assignee: Eurosets S.r.l., Medolla (IT)

( * ) Notice: Subject to any disclaimer, the term of this patent is extended or adjusted under 35 U.S.C. 154(b) by 0 days.

(21) Appl. No.: 11/802,594

(22) Filed: May 24, 2007

(65) Prior Publication Data

US 2007/0293805 A1   Dec. 20, 2007

(30) Foreign Application Priority Data

Jun. 20, 2006   (IT) .......................... MI2006A1187

(51) Int. Cl.
*A61M 37/00*   (2006.01)

(52) U.S. Cl. .................... 604/6.09; 604/6.11; 604/6.15; 604/4.01

(58) Field of Classification Search ................ 604/6.14, 604/6.11, 6.09, 6.15, 4.01
See application file for complete search history.

(56) References Cited

U.S. PATENT DOCUMENTS

| | | | | |
|---|---|---|---|---|
| 4,061,470 A | * | 12/1977 | Leonard | 422/48 |
| 4,228,125 A | * | 10/1980 | Lobdell et al. | |
| 4,680,115 A | * | 7/1987 | LaValley | 210/247 |
| 4,737,139 A | * | 4/1988 | Zupkas et al. | |
| 5,158,533 A | * | 10/1992 | Strauss et al. | |
| 5,304,164 A | * | 4/1994 | Lindsay | 604/403 |
| 5,772,970 A | * | 6/1998 | Okamoto | 422/191 |
| 5,849,186 A | * | 12/1998 | Raneri et al. | 210/315 |
| 6,322,546 B1 | * | 11/2001 | Steg | 604/319 |
| 6,428,747 B1 | * | 8/2002 | Dueri et al. | 422/46 |
| 6,689,315 B2 | * | 2/2004 | Linker et al. | 422/45 |
| 6,730,267 B2 | * | 5/2004 | Stringer et al. | 422/45 |
| 6,773,670 B2 | * | 8/2004 | Stringer et al. | 422/44 |
| D515,419 S | * | 2/2006 | Manke | D9/447 |
| 6,998,093 B1 | * | 2/2006 | McIntosh et al. | 422/45 |
| 7,541,000 B2 | * | 6/2009 | Stringer et al. | 422/45 |
| 2002/0110485 A1 | * | 8/2002 | Stringer et al. | 422/45 |
| 2002/0114731 A1 | * | 8/2002 | Stringer et al. | 422/44 |
| 2004/0009097 A1 | * | 1/2004 | Stringer et al. | 422/45 |
| 2005/0209555 A1 | * | 9/2005 | Middleton et al. | 604/82 |

FOREIGN PATENT DOCUMENTS

| | | | |
|---|---|---|---|
| EP | 0 320 815 A2 | * | 6/1989 |
| EP | 1 344 543 A1 | * | 9/2003 |
| WO | WO 98/20957 A | * | 5/1998 |

* cited by examiner

*Primary Examiner*—Tatyana Zalukaeva
*Assistant Examiner*—Susan Su
(74) *Attorney, Agent, or Firm*—Modiano & Associati; Albert Josif; Daniel J. O'Byrne

(57) ABSTRACT

A venous reservoir in an extracorporeal blood circuit, comprising a rigid outer enclosure for a filtering mass in the form of a hollow cylinder, provided with an upper lid which comprises couplings for the inflow of blood with the portion of space delimited by the filtering mass and with a connector at the bottom, the reservoir further comprising a diaphragm which is arranged below the upper lid and is adapted to receive the blood that enters through the couplings provided in the peripheral region of the lid, at the axis of a central hole of the diaphragm there is a column with longitudinal vanes which protrude upwardly until they skim the rim of the hole and are adapted to follow the blood in its flow by gravity toward the collection region at the base of the enclosure.

2 Claims, 3 Drawing Sheets

VENOUS RESERVOIR IN AN EXTRACORPOREAL BLOOD CIRCUIT

The present invention relates to a venous reservoir in an extracorporeal blood circuit.

BACKGROUND OF THE INVENTION

It is known that one of the devices present in extracorporeal blood circuits established during certain surgical procedures is a container provided with a rigid enclosure which is designed to receive blood at couplings provided on the upper lid and connected to several lines that arrive for example from a drain of the arterial filter or a sampling tap, or also from a cannula known as "intracavitary" cannula, which is connected directly to the heart of the patient, and further, at a connector at the bottom which comprises two couplings which are connected to blood intake lines, which arrive respectively from a vein of the patient and from a vessel known as cardiotomy reservoir, which receives and filters the blood collected in the operating field.

Such container is indeed known as "venous reservoir".

SUMMARY OF THE INVENTION

The aim of the present invention is to provide a venous reservoir in which the incoming blood, and in particular the blood that arrives from the couplings provided on the upper lid, reaches the collection region proximate to the bottom nontraumatically.

This aim is achieved by a venous reservoir in an extracorporeal blood circuit according to the invention, comprising a rigid outer enclosure which is adapted to contain a filtering mass in the form of a hollow cylinder, provided with an upper lid which comprises a plurality of couplings for the inflow of blood and connected to the portion of space delimited by said filtering mass, and further provided with a connector at the bottom which is connected to said portion of space and comprises two couplings for connection to blood inflow lines which arrive respectively from the patient and from a cardiotomy reservoir, characterized in that it comprises:

- a diaphragm which is arranged below the upper lid and is adapted to receive the blood that enters through couplings provided in the peripheral region of the lid with such flow conditions as to have no component which is perpendicular to said diaphragm, and comprising a central hole which is provided at the edge with a plurality of screens which are adapted to direct the blood which flows on the diaphragm so that it enters said hole;
- a column, which is arranged at the axis of the central hole of the diaphragm, is provided with longitudinal vanes which protrude upwardly until they skim the rim of said hole and are adapted to follow the blood in its flow by gravity towards the collection region at the base of the enclosure, said column being provided at the top with a protrusion which faces the direct vicinity of the outlet of a coupling provided in the central region of the lid, so as to follow the blood which enters through said coupling and flows by gravity on the wall of said protrusion until it comes into contact with said vanes.

BRIEF DESCRIPTION OF THE DRAWINGS

Further characteristics and advantages of the present invention will become better apparent from the description of a preferred but not exclusive embodiment thereof, illustrated by way of non-limiting example in the accompanying drawings, wherein.

DESCRIPTION OF THE PREFERRED EMBODIMENTS

Figure 1:
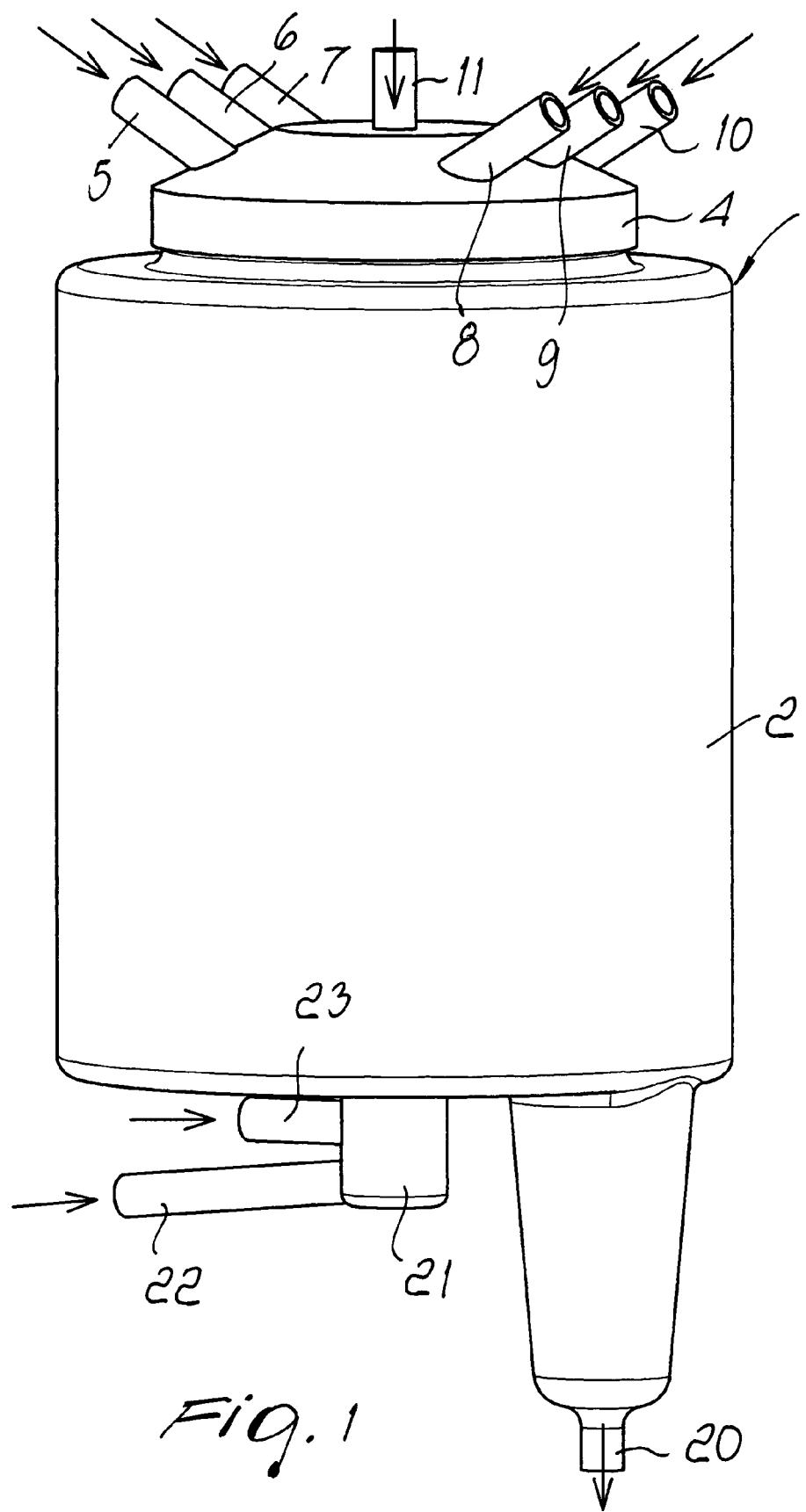
FIG. 1 is a perspective view of the venous reservoir according to the invention.

With reference to the figures, the reference numeral 1 generally designates a venous reservoir which comprises a rigid outer enclosure 2, which contains a filtering mass 3 in the form of a hollow cylinder.

An upper lid 4 of the enclosure 2 is provided with couplings 5, 6, 7, 8, 9, 10 which are adapted to be connected to lines for conveying blood from different points to the reservoir, which are arranged in the peripheral region of the lid, and is further provided with a central coupling 11, which is adapted to be connected preferably to the intracavitary aspiration cannula.

Figure 2:
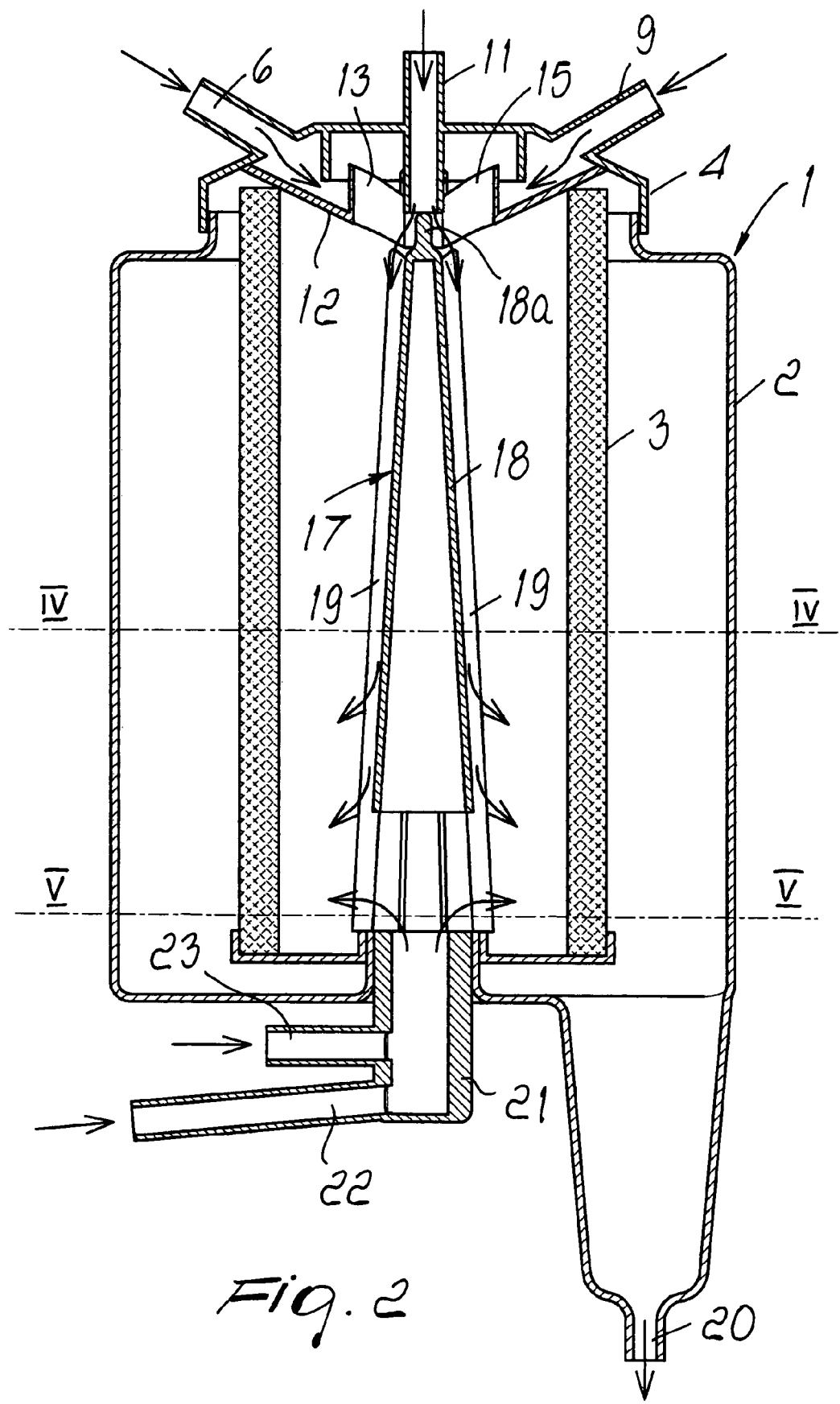
FIG. 2 is a longitudinal sectional view thereof.
Figure 3:
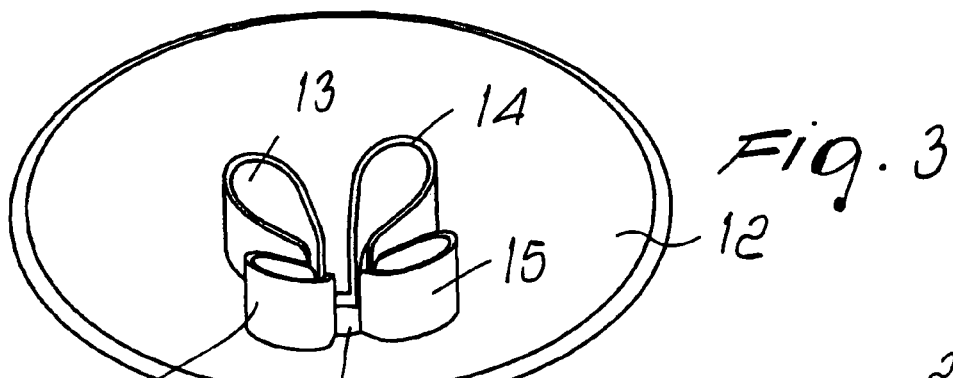
FIG. 3 is a perspective view of the diaphragm.
Figure 4:
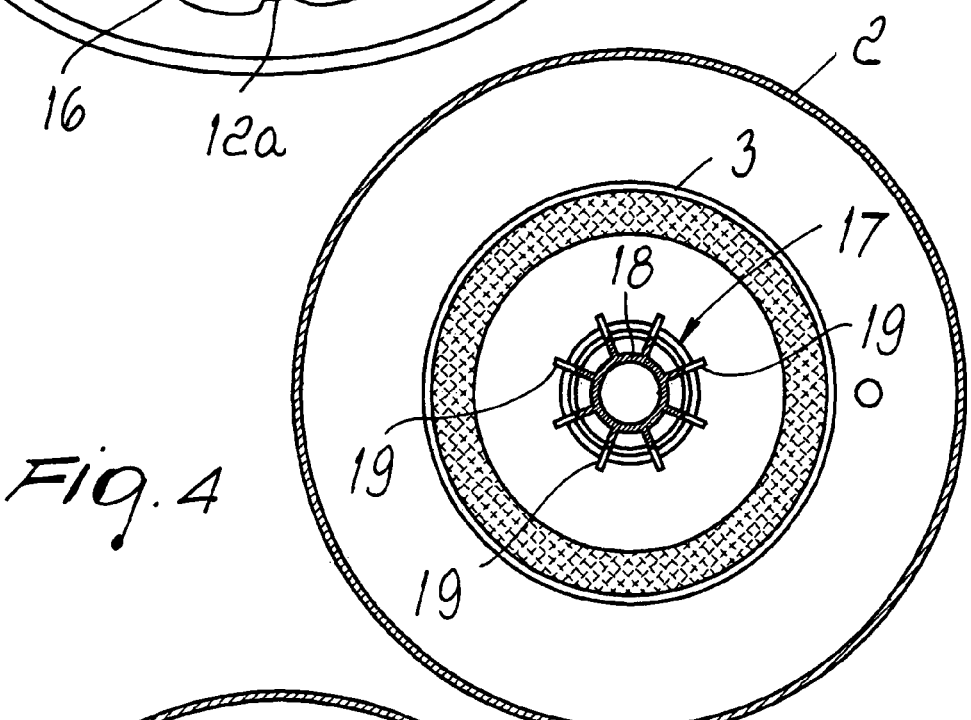
FIGS. 4 and 5 are respectively sectional views taken along the lines IV-IV and V-V of FIG. 2.
Figure 5:
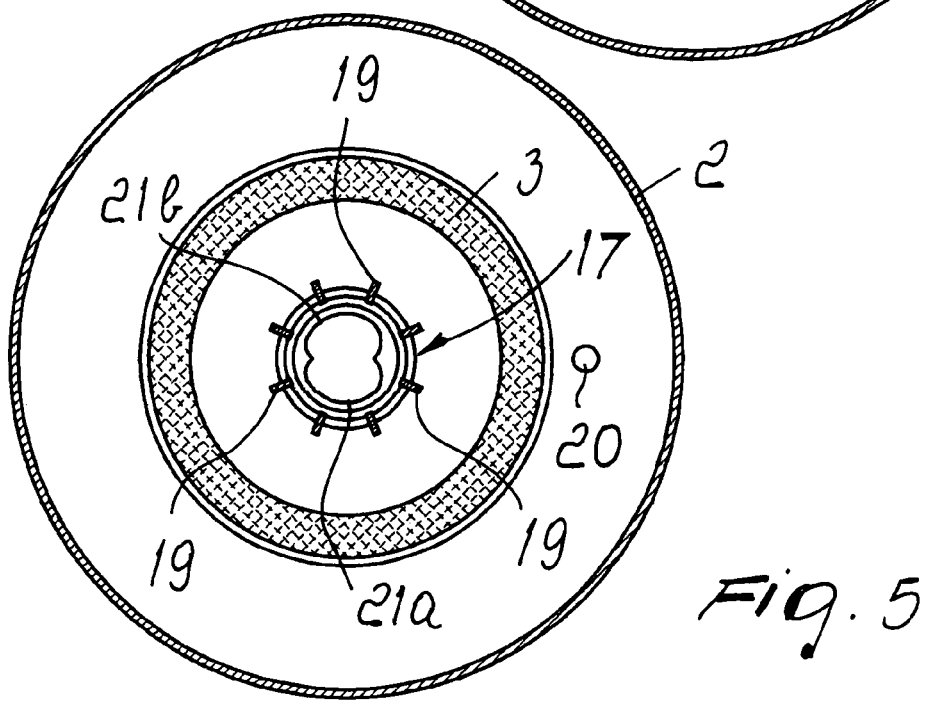

Below the lid 4 a diaphragm 12 is provided, which is contoured so that it can receive, as shown by the arrows of FIG. 2, the blood that enters through the couplings of the peripheral region of the lid with such flow conditions as to have no component which is perpendicular to said diaphragm, and said diaphragm comprises a central hole 12a which has, at its edge, four screens 13, 14, 15, 16, which are adapted to direct the blood that flows onto the diaphragm 12 so that it enters the hole 12a.

The reference numeral 17 generally designates a column which is arranged at the axis of the hole 12a and comprises a conical body 18, which is interrupted proximate to the base and is provided with longitudinal vanes 19, which protrude radially from the body 18, extending downwardly, at least partly, to the bottom of the enclosure and upwardly so as to skim the rim of the hole 12a, so as to receive in contact the blood which flows by gravity through the screens 13, 14, 15, 16 substantially when it leaves contact with the diaphragm 12 to follow it in its downward motion to the collection region located proximate to the bottom of the enclosure 2, so as to provide a blood flow condition which ensures the fullest lack of traumas and inclusion of air to the blood.

A protrusion 18a is provided at the top of the body 18 of the column 17 and faces, by passing through the hole 12a, the direct vicinity of the outlet of the coupling 11, so as to follow the blood which enters from the coupling so that it flows in contact with its wall until it comes into contact with the vanes 19 in order to be guided thereby downwardly completely without traumas and air inclusion, all as shown by the arrows in FIG. 2.

At the bottom of the enclosure 2, where a hole 20 for the exit of the blood from the reservoir is provided, there is a connector 21, which comprises two couplings 22, 23 adapted to be connected to lines for the inflow of blood into the reservoir which arrive respectively from the patient and from a cardiotomy reservoir; the wall of the blood passage port is shaped like two lobes 21a, 21b which determine a uniform distribution of the flow of blood which enters the reservoir from the bottom, shown by the arrows of FIG. 2.

The described invention is susceptible of numerous modifications and variations, all of which are within the scope of the appended claims; all the details may further be replaced with other technically equivalent elements.

The disclosures in Italian Patent Application No. MI2006A001187 from which this application claims priority are incorporated herein by reference.

What is claimed is:

1. A venous reservoir for an extracorporeal blood circuit, comprising:

a rigid outer enclosure which contains a filtering mass in the form of a hollow cylinder, an upper lid which comprises a plurality of couplings for the inflow of blood and connected to a portion of space delimited by said filtering mass, an inflow connector at a bottom which is connected to said portion of space and comprises two couplings for connection to blood inflow lines which arrive respectively from a patient and from a cardiotomy reservoir, a diaphragm which is arranged below the upper lid and is adapted to receive the blood that enters through said couplings provided in a peripheral region of the lid with such flow conditions as to have no component which is perpendicular to said diaphragm, and comprising a central hole which is provided with, at an edge of said central hole, a plurality of screens which are adapted to direct the blood which flows on the diaphragm so that it enters said central hole;

a column, which is arranged at an axis of the central hole of the diaphragm, is provided with longitudinal vanes which protrude upwardly until they skim a rim of said central hole and are adapted to follow the blood in its flow by gravity towards a collection region at a base of the enclosure, said column being provided at a top with a protrusion which faces a direct vicinity of an outlet of a central coupling in the central region of the lid, so as to follow the blood which enters through said central coupling and flows by gravity on a wall of said protrusion until said blood comes into contact with said vanes.

2. The reservoir according to claim 1, wherein to blood inflow connector at a bottom has a lobe-shaped passage port wall.

* * * * *